United States Patent [19]

Wayman

[11] Patent Number: 4,736,762

[45] Date of Patent: Apr. 12, 1988

[54] ANTI-CONTAMINATION MEANS

[76] Inventor: Joseph R. Wayman, 3001 Dorner Cir., Raleigh, N.C. 27606

[21] Appl. No.: 809,135

[22] Filed: Dec. 16, 1985

[51] Int. Cl.⁴ ..................... E04H 15/06; A61B 19/00; A61G 10/00

[52] U.S. Cl. ...................................... 135/88; 135/106; 128/1 B; 128/205.26; 296/19; 296/39 R; 52/2

[58] Field of Search ..................... 135/106, 88, 90, 91, 135/89, 87; 128/18, 202.16, 205.26; 296/19, 24 R, 39 R, 97 D; 52/2

[56] References Cited

U.S. PATENT DOCUMENTS

| | | | |
|---|---|---|---|
| 2,401,230 | 5/1946 | Colley | 128/205.26 X |
| 2,895,490 | 7/1959 | Dimond | 135/106 X |
| 3,432,609 | 3/1969 | DuVall et al. | 52/2 X |
| 3,602,221 | 8/1971 | Bleicken | 128/205.26 |
| 3,729,002 | 4/1973 | Miller | 128/205.26 |
| 4,093,302 | 6/1978 | Adams | 135/88 X |
| 4,296,960 | 10/1981 | Winchester | 135/88 X |
| 4,469,732 | 9/1984 | Isaksen et al. | 296/39 R X |
| 4,516,906 | 5/1985 | Krein | 296/39 R X |
| 4,568,028 | 2/1986 | Verseef et al. | 296/39 R X |

FOREIGN PATENT DOCUMENTS

| | | | |
|---|---|---|---|
| 107372 | 5/1939 | Australia | 128/205.26 |
| 639062 | 3/1962 | Canada | 52/2 |
| 0036051 | 9/1981 | European Pat. Off. | 52/2 |
| 2043737 | 10/1980 | United Kingdom | 52/2 |
| 2117716 | 10/1983 | United Kingdom | 296/39 R |

*Primary Examiner*—Robert A. Hafer
*Assistant Examiner*—D. Neal Muir
*Attorney, Agent, or Firm*—Rhodes, Coats & Bennett

[57] ABSTRACT

This invention is an inflatable, anti-contamination enclosure for use in connection with emergency vehicles for transporting contaminated casualties from an accident site to medical facilities. The enclosure may be rolled up and stored in a convenient place when not in use. When needed, the enclosure can be rolled out on the floor of the emergency vehicle. As the enclosure is inflated, adhesive strips on the outside of the enclosure are exposed to secure the same against the top and side of the emergency vehicle. All openings into the enclosure are provided with flaps having a fabric loop and hook material for securing the same.

2 Claims, 3 Drawing Sheets

ANTI-CONTAMINATION MEANS

FIELD OF INVENTION

The invention relates to inflatable enclosures, and more particularly to a method and apparatus for handling and transporting contaminated individuals.

BACKGROUND OF INVENTION

Now, more than ever before in history, people are at a risk of being accidentally exposed to radioactive and toxic substances. The widespread use of nuclear power plants for the generation of electricity presents a potential risk of accidental exposure to virtually everyone, not just those who work in or live near those plants. Nuclear fuel and waste products are commonly transported over highways. A single accident is capable of widespread contamination. Moreover, there is no assuredly safe method for disposing of nuclear waste.

The problem, however, is not limited to the nuclear industry. Many industries use highly toxic substances to manufacture goods. Like nuclear fuel and waste, these toxic substances are transported over highways. The problem of disposing of these substances is particularly acute and the number of hazardous waste sites is increasing at a rapid pace.

Despite the high risk of accidental exposure to radioactive and toxic substances, the medical profession is ill equiped to handle contaminated casualties. In particular, there is no clean method for transporting contaminated casualties from the scene of an accident to medical facilities. The transport of contaminated individuals inevitably results in contamination of expensive medical equipment and even the emergency vehicle itself.

Once contaminated, medical equipment must frequently be discarded. The vehicle itself must also go through time consuming and expensive decontamination procedures. Even then, there is no guarantee that radioactive and toxic substances can be adequately removed to allow the vehicle to return to service.

SUMMARY AND OBJECTS OF INVENTION

After much research and study into the above mentioned problems, the present invention has been developed to provide a simple, cost effective means for retaining radioactive and toxic particles during transportation of a contaminated individual or individuals to medical facilities.

The above is accomplished through the provision of an inflatable enclosure which can be rolled up during storage. When needed, the enclosure can be rolled out on the floor of the emergency vehicle. As the enclosure is inflated, adhesive strips on the outside of the enclosure are exposed to hold the same against the inside top of the emergency vehicle. All openings into the enclosure are provided with flaps for preventing the escape of contaminated particles.

In view of the above, it is an object of the present invention to provide an anti-contamination enclosure for use in transporting contaminated casualties to medical facilities.

Another object of the present invention is to provide an anti-contamination enclosure which can be inserted into an emergency rescue vehicle.

Another object of the present invention, is to provide an anti-contamination enclosure which may be rolled up and stored when not in use.

Another object of the present invention is to provide an anti-contamination enclosure which can be easily and quickly inflated when needed.

Another object of the present invention is to provide an anti-contamination enclosure which can be easily and inexpensively manufactured and used.

Other objects and advantages of the present invention will become apparent and obvious from a review of the detailed description of the invention and the accompanying drawings.

DETAILED DESCRIPTION OF THE INVENTION

Figure 1:
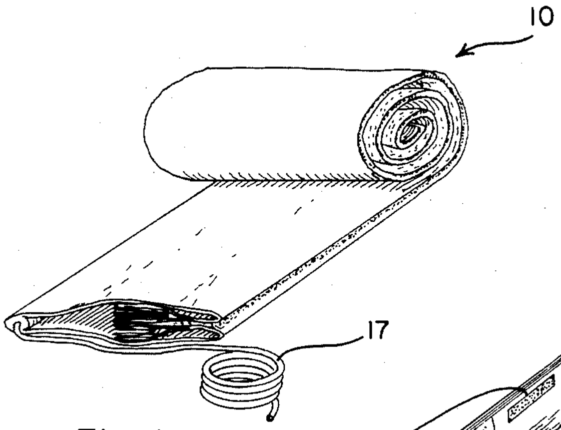
FIG. 1 is a perspective view of the enclosure of the present invention when it is rolled up for storage.

With further reference to the drawings, the anti-contamination enclosure of the present invention, indicated generally at 10, includes a bottom 11, side walls 12, a front wall 13, and a top 14, all integrally formed to provide an air tight, leak proof enclosure.

The bottom 11 is generally rectangular in configuration and can be formed from a nylon reinforced material such as herculite. The side walls 12, the front wall 13, and the top 14 are all constructed from a flexible material such as plastic, rubber, neoprene or other impervious material and, as mentioned above, are integral with bottom 11.

Running longitudinally the length of top 14 is a central manifold 15. A plurality of laterally disposed inflatable support tubes 16 communicate with central manifold 15 and extend across the top 14 and down side walls 12 to a point adjacent bottom 11 as can clearly be seen in FIGS. 3 and 4.

An inflating hose 17 is connected at one end to the end of central manifold 15 and communicates therewith. The other end of inflating hose 17 is adapted to be connected to a source of compressed air 21 such as a compressed air tank, a $CO_2$ inflating means, a compressor, or the like. Since inflating means of this type are well known to those skilled in the art, further detailed discussion of the same is not deemed necessary.

A plurality of securing means 18 are provied in spaced relationship along the upper surface of top 14. These securing means are preferably strips of adhesive material as illustrated at 19. During storage, a protective strip 20 is used to protect and isolate the adhesive surface. Adhesive strips and the protective surfaces provided with the same are well known to those skilled in the art and further detailed discussion of the same is not deemed necessary.

A pair of closure curtains 22 are integrally formed along the rear edge of each of the two side walls 12. These curtains are formed from the same type of material as the side walls and include fastening means 23 such as velcro type material along the upper edges of such curtains where they join the end of top portion 14.

Figure 6:
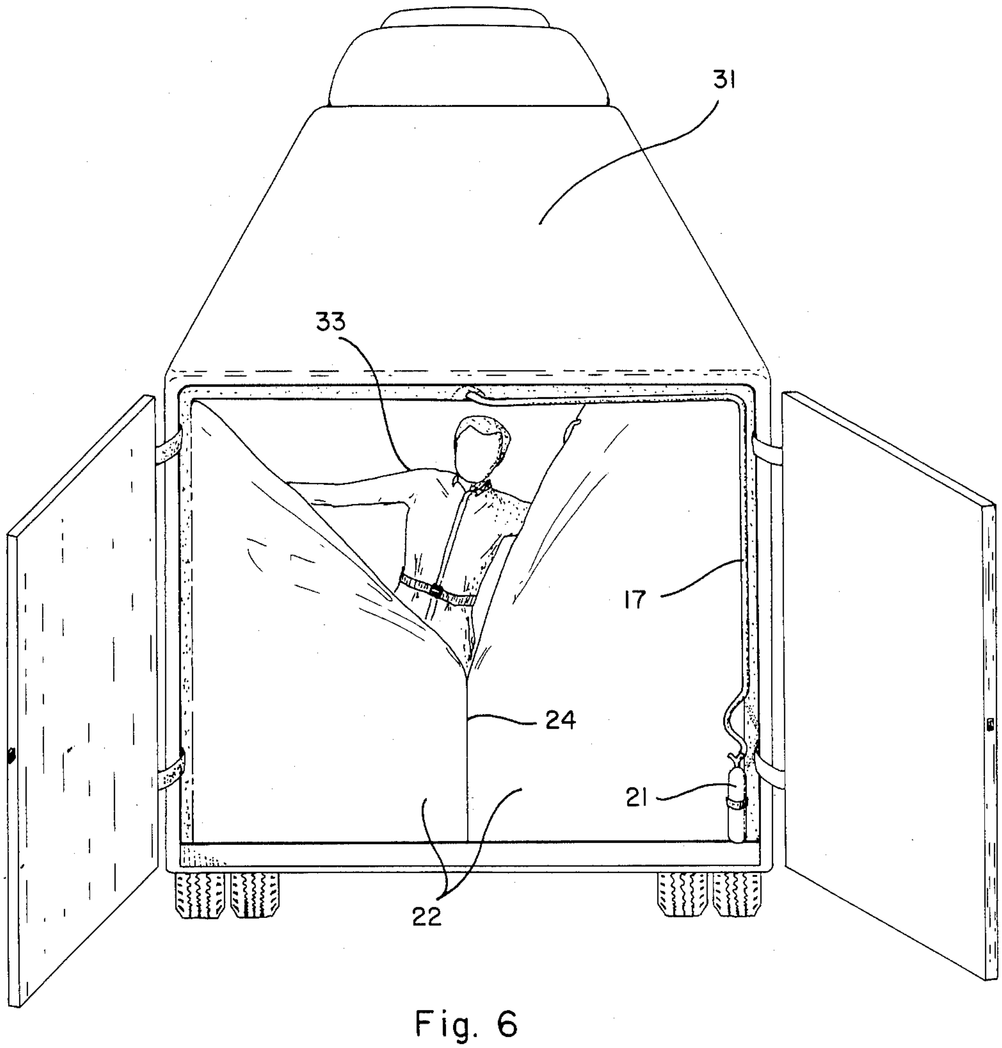
FIG. 6 is an exterior perspective view of an emergency vehicle having the enclosure therein.

Velcro type securing means 24 is also preferably used in joining the two closure curtains 22 as clearly shown in FIG. 6.

An interior flap 25 is integrally formed with bottom 11 and the lower portion of side walls 12 adjacent gussets 26. The outer or upper edge of flap 25 includes a securing means 27 such as velcro which is adapted to secure such flap to the interior of the closure curtains 22 at a point above bottom 11 as can clearly be seen in FIG. 5.

If desired, one or more windows 27 can be provided in side walls 12 and/or top 14 to admit light and to allow the people in the enclosure to see out. This window or windows are formed from a flexible plastic material and, of course, would be integral with the adjacent wall and/or top.

A flexible window cover flap 28 is be provided for window 27. Again velcro, as indicated at 29, is the preferred securing means for the window cover.

A plurality of storage pockets 30 are provided along the interior of side walls 12. These pockets would, of course, be formed from a flexible material to facilitate folding of the enclosure of the present invention when not in use.

The anti-contamination enclosure 10 of the present invention is folded and rolled into a compact configuration for transportation and storage prior to use. This compact storage is an advantage since the enclosure can be stored out of the way in the emergency vehicle and carried as standard equipment so as to be readily available when needed.

Figure 2:
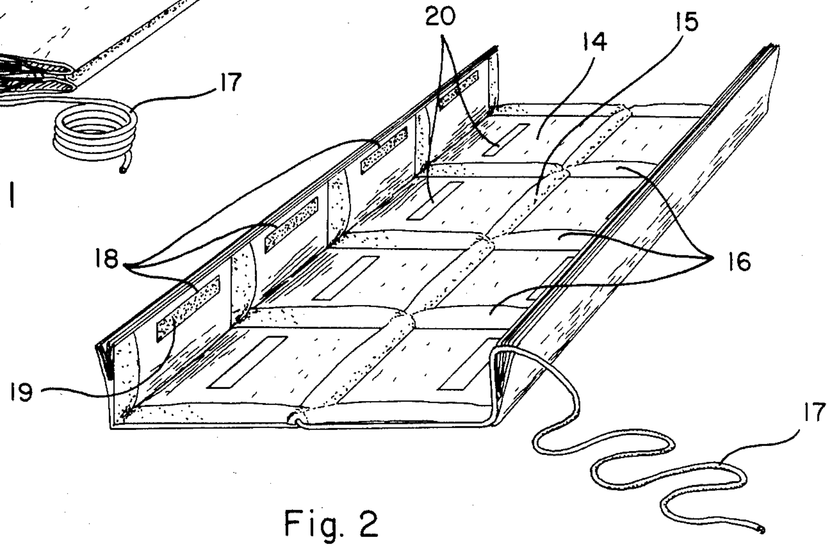
FIG. 2 is a perspective view of the enclosure when it is unrolled, but before it is inflated.

When it is desired to use the anti-contamination enclosure 10 of the present invention, the same is placed on the floor of the emergency vehicle and rolled out to a flat position. The enclosure is then unfolded to the point shown in FIG. 2 and the protective surface 20 removed from the adhesive strips 19.

Figure 3:
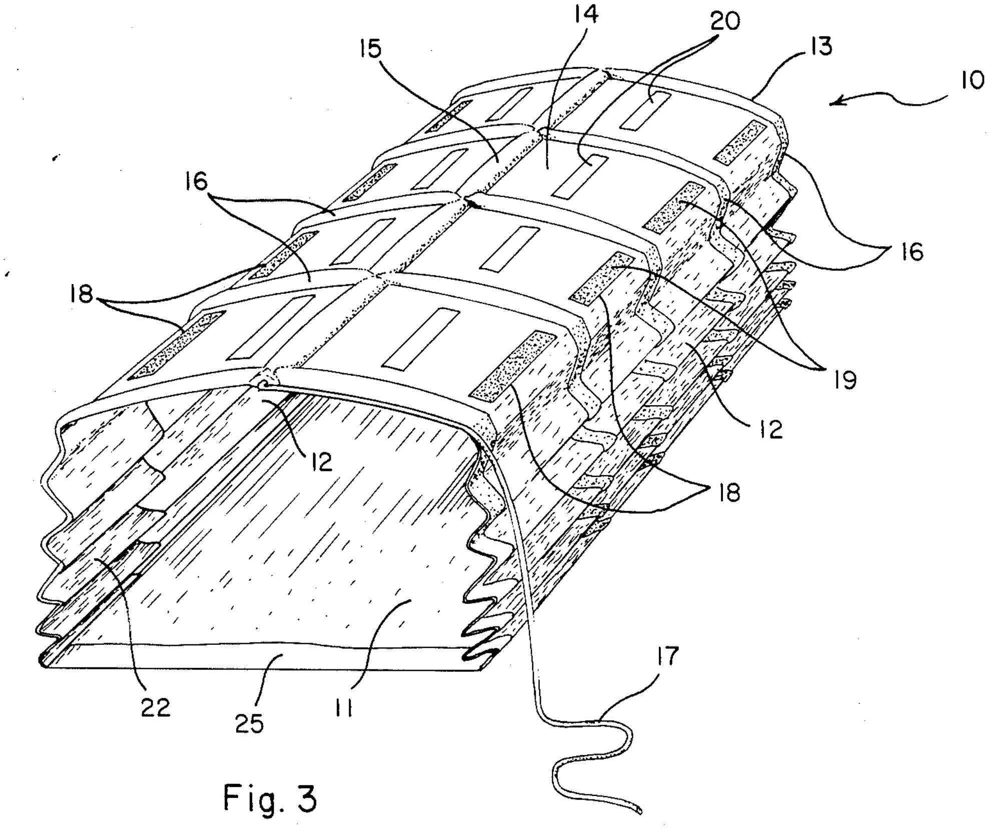
FIG. 3 is a perspective view of the enclosure as it is being inflated.

A fluid such as compressed air is then passed through inflating hose 17 from a source such as compressed air tank 21. As the fluid enters the central manifold 15, such fluid inflates the same and in turn the fluid passes from the manifold into the inflatable support tubes 16 inflating these also. As the inflation process progresses, the accordion folded sides 12 begin to extend as shown in FIG. 3.

Figure 4:
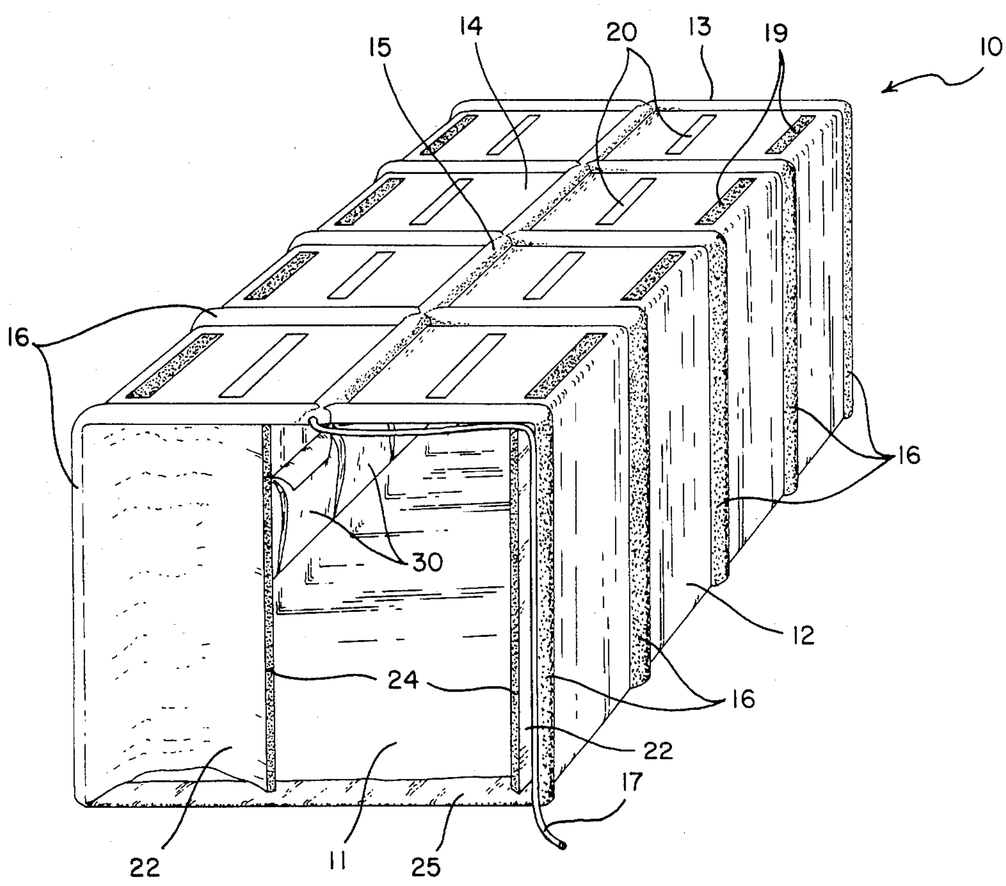
FIG. 4 is an exterior perspective view of the fully inflated enclosure.

Once all the support tubes 16 of the enclosure 10 of the present invention have become fully inflated, such enclosure is deployed as shown in FIG. 4. At this point the exposed adhesive surfaces 19 can be pressed from inside the enclosure against the interior roof of the emergency vehicle 31 to adhere the anti-contamination enclosure to such vehicle. This prevents sagging from occuring in the enclosure during use as well as preventing complete collapse of such enclosure should the manifold or one or more of the support tubes become ruptured or otherwise punctured causing loss of internal pressure.

Once the anti-contamination enclosure 10 has been deployed within the emergency vehicle 31 as described above, it is ready to receive contaminated casualties.

When the casualty or casualties have been loaded into the enclosure disposed within the emergency vehicle, the emergency medical personnel will pull the closure curtains 22 across the rear open end of the enclosure 10 as illustrated in FIG. 6. The velcro securing means 23 will secure the upper edges of the closure curtains 22 to the rear edge of top 14. The closure curtains themselves will then be pressed together with velcro 24 acting to secure the same.

Figure 5:
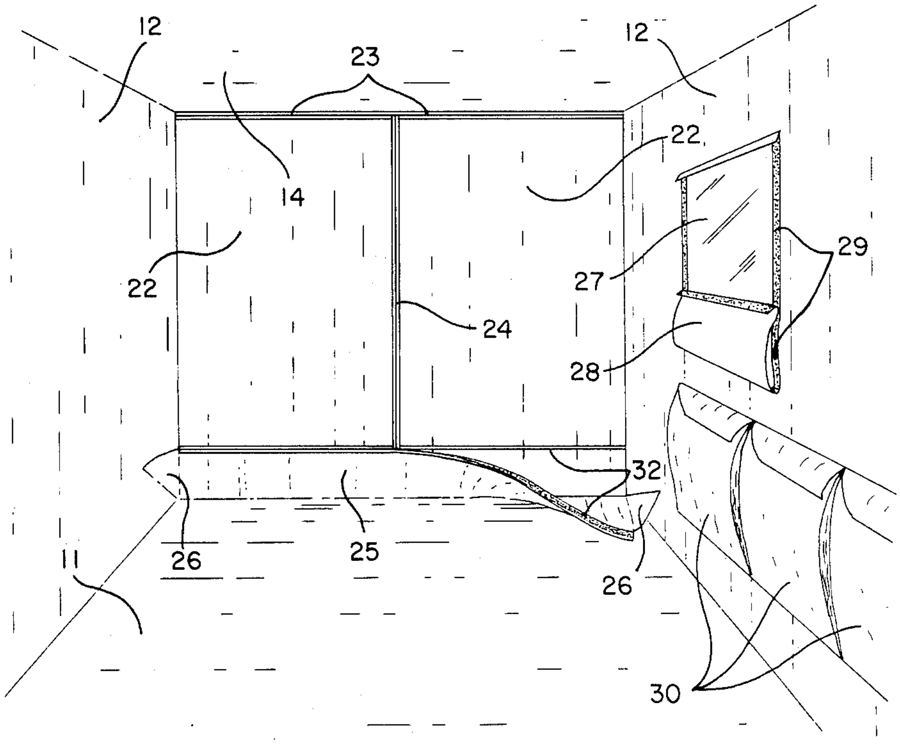
FIG. 5 is an exterior perspective view of the fully inflated enclosure.

The anti-contamination flap 25 is then folded up along the interior of closure curtains 22 and is secured in place by velcro 32. The gussets 26 on either end of flap 25 allow such flap to be folded down juxtaposed to floor 11 during loading and unloading of patients while at the same time eliminating contamination seepage around the edges of such flap when in place as shown in FIG. 5.

The windows 27 and their associated closure flaps 28 as well as the storage pockets 30 are used as desired by the emergency medical personnel 33.

Whenever the transportation of the contaminated casualties has been completed, clean up of the emergency vehicle 31 is simple to accomplish when inflation hose 17 is opened to deflate the central manifold 15 and the inflatable support tube 16. The securing means 18 are then separated from the interior roof of vehicle 31 and the entire enclosure 10 folded down and removed from such vehicle.

If the contamination is of such a nature that the enclosure cannot be readily decontaminated, the same can be disposed of in the normal manner of contaminated articles. Also, the relatively low cost of the enclosure of the present invention can be weighed against the decontamination procedures and the most cost efficient choice can be selected.

In other words, depending upon the type of contamination and the difficulty in decontaminating the enclosure, it can be cleaned for reuse or disposed of. In either case, expensive clean up and decontamination of the emergency vehicle has been eliminated at the relatively low cost of the enclosure or the cleaning of the same.

The present invention has the advantage of being relatively inexpensive to produce, can be compactly stored until needed, and is easy to deploy. The enclosure likewise is easy to remove from the emergency vehicle after use and can be either decontaminated for reuse or disposed of as appropriate.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An apparatus for transporting contaminated persons comprising:

(a) a self-propelled vehicle having an enclosed vehicle compartment for transporting persons;

(b) enclosure means formed with a liquid impervious sheet material disposed within said vehicle compartment and having a generally retangular configuration including one sealed end and one open end through which said enclosure means may be entered;

(c) said enclosure means further including an inflatable support structure for supporting said liquid impervious sheet material including a series of parallel, inflatable tubes and a maniford feed interconnecting said parallel tubes; and (d) closure means comprising door members extending from sides of said rectangular configuration adjacent said open end formed with a liquid impervious sheet material for sealing said open end of said enclosure means when said enclosure is in an inflated condition, so that upon inflation an enclosure, hermetically sealed at ambient pressures, is formed within said vehicle compartment.

2. The anti-contamination means of claim 1 wherein said enclosure means includes accordion-like side walls having a plurality of parallel folds, said parallel folds extending longitudinally along the length of said anti-contamination means generally perpendicular to the inflatable tube.

* * * * *